US008692043B2

(12) United States Patent
Lauritzen et al.

(10) Patent No.: US 8,692,043 B2
(45) Date of Patent: Apr. 8, 2014

(54) PROCESS FOR THE CONVERSION OF ETHANE TO AROMATIC HYDROCARBONS

(75) Inventors: Ann Marie Lauritzen, Houston, TX (US); Ajay Madhav Madgavkar, Katy, TX (US)

(73) Assignee: Shell Oil Company, Houston, TX (US)

(*) Notice: Subject to any disclaimer, the term of this patent is extended or adjusted under 35 U.S.C. 154(b) by 663 days.

(21) Appl. No.: 12/867,973

(22) PCT Filed: Feb. 18, 2009

(86) PCT No.: PCT/US2009/034364
§ 371 (c)(1),
(2), (4) Date: Oct. 7, 2010

(87) PCT Pub. No.: WO2009/105447
PCT Pub. Date: Aug. 27, 2009

(65) Prior Publication Data
US 2011/0021853 A1    Jan. 27, 2011

Related U.S. Application Data

(60) Provisional application No. 61/029,939, filed on Feb. 20, 2008.

(51) Int. Cl.
*C07C 2/02* (2006.01)
(52) U.S. Cl.
USPC .......... 585/417; 585/407; 585/415; 585/418; 585/419
(58) Field of Classification Search
USPC ..................... 585/407, 415, 417, 418, 419
See application file for complete search history.

(56) References Cited

U.S. PATENT DOCUMENTS

| | | | |
|---|---|---|---|
| 3,827,867 A | 8/1974 | Heinemann et al. | |
| 4,058,452 A | 11/1977 | Loboda | |
| 4,100,218 A | 7/1978 | Chen et al. | |
| 4,120,910 A | 10/1978 | Chu | 260/673 |
| 4,158,026 A | 6/1979 | Addison | |
| 4,215,231 A | 7/1980 | Raymond | |
| 4,229,602 A | 10/1980 | Brinkmeyer et al. | 585/407 |
| 4,528,412 A | 7/1985 | Steacy | 585/415 |
| 4,547,205 A | 10/1985 | Steacy | 55/25 |
| 4,642,402 A | 2/1987 | Jensen | 585/411 |
| 4,677,235 A | 6/1987 | Mowry | 585/415 |
| 4,766,265 A | 8/1988 | Desmond et al. | 585/415 |
| 4,806,699 A | 2/1989 | Smith et al. | 585/314 |
| 4,806,700 A | 2/1989 | Martindale | 585/322 |
| 4,855,522 A | 8/1989 | Diaz | 585/417 |
| 4,968,401 A | 11/1990 | Harandi et al. | 208/49 |
| 4,996,381 A | 2/1991 | Pickering, Jr. et al. | 585/413 |
| 5,013,423 A | 5/1991 | Chen et al. | |
| 5,019,663 A | 5/1991 | Chou et al. | 585/415 |
| 5,026,937 A | 6/1991 | Bricker | 585/415 |
| 5,030,782 A | 7/1991 | Harandi et al. | 585/322 |
| 5,053,570 A | 10/1991 | Soto et al. | 585/417 |
| 5,186,908 A | 2/1993 | Nemet-Mavrodin et al. | 422/190 |
| 5,210,350 A | 5/1993 | Solofo et al. | |
| 5,215,950 A | 6/1993 | Bouronville et al. | 502/66 |
| 5,227,557 A | 7/1993 | Bouronville et al. | 585/419 |
| 5,258,563 A | 11/1993 | Gosling et al. | 585/322 |
| 5,386,071 A | 1/1995 | Kuchar et al. | 585/313 |
| 5,456,822 A | 10/1995 | Marcilly et al. | 208/136 |
| 5,932,777 A | 8/1999 | Sughrue, II et al. | |
| 5,936,135 A | 8/1999 | Choudhary et al. | 585/418 |
| 6,143,941 A | 11/2000 | Sharma et al. | 585/481 |
| 6,635,792 B2 | 10/2003 | Choi et al. | 585/489 |
| 7,019,184 B2 | 3/2006 | Allison et al. | 585/415 |
| 7,186,871 B2 | 3/2007 | Mitchell et al. | 585/418 |
| 2003/0036670 A1 | 2/2003 | Oh et al. | 585/400 |
| 2004/0020827 A1 | 2/2004 | Elomari | |
| 2004/0028584 A1 | 2/2004 | Juttu et al. | 423/64 |
| 2005/0143610 A1 | 6/2005 | Mitchell et al. | 585/418 |
| 2006/0287564 A1 | 12/2006 | Choi et al. | 585/489 |
| 2008/0293980 A1 | 11/2008 | Kiesslich et al. | |

FOREIGN PATENT DOCUMENTS

| | | | |
|---|---|---|---|
| CA | 2620480 | 4/2007 | C07C 2/76 |
| EP | 50021 | 4/1982 | C07C 2/76 |
| EP | 0147111 | 3/1985 | |
| EP | 244162 | 11/1987 | C07C 2/76 |
| EP | 493040 | 7/1992 | C10G 35/06 |
| EP | 512912 | 11/1992 | B01J 8/06 |
| EP | 1001001 | 5/2000 | |
| GB | 1442850 | 7/1976 | C07C 3/00 |
| WO | WO2004025767 | 3/2004 | H01M 8/06 |
| WO | WO2004076346 | 9/2004 | |
| WO | WO2007048853 | 3/2007 | C07C 2/84 |
| WO | WO2007037866 | 4/2007 | B01J 29/06 |
| WO | WO2007117406 | 10/2007 | C10G 35/04 |
| WO | WO2007144324 | 12/2007 | C07C 2/76 |

OTHER PUBLICATIONS

Waku et al., "Catalytic dehydrogenation of alkanes on Pt/Na-[Fe]ZSM5 and staged O2 introduction for selective H2 removal", Journal of Catalysis, 222, 2004, pp. 481-492.*

* cited by examiner

*Primary Examiner* — Elizabeth Wood

(57) ABSTRACT

A process for producing aromatic hydrocarbons which comprises (a) contacting ethane with a dehyroaromatization aromatic catalyst which is comprised of 0.005 to 0.1% wt platinum, an amount of iron which is equal to or greater than the amount of the platinum, from 10 to 99.9% wt of an aluminosilicate, and a binder, and (b) separating methane, hydrogen, and $C_{2-5}$ hydrocarbons from the reaction products of step (a) to produce aromatic reaction products including benzene.

11 Claims, No Drawings

US 8,692,043 B2

PROCESS FOR THE CONVERSION OF ETHANE TO AROMATIC HYDROCARBONS

PRIORITY CLAIM

The present application claims priority to US Provisional Patent Application No. 61/029,939 filed 20 Feb. 2008.

FIELD OF THE INVENTION

The present invention relates to a process for producing aromatic hydrocarbons from ethane. More specifically, the invention relates to a dehydroaromatization process for increasing the production of benzene and/or total aromatics from ethane.

BACKGROUND OF THE INVENTION

There is a projected global shortage for benzene which is needed in the manufacture of key petrochemicals such as styrene, phenol, nylon and polyurethanes, among others. Generally, benzene and other aromatic hydrocarbons are obtained by separating a feedstock fraction which is rich in aromatic compounds, such as reformates produced through a catalytic reforming process and pyrolysis gasolines produced through a naphtha cracking process, from non-aromatic hydrocarbons using a solvent extraction process.

In an effort to meet growing world demand for benzene and other aromatics, various industrial and academic researchers have been working for several decades to develop catalysts and processes to make light aromatics (benzene, toluene, xylenes, or BTX) from cost-advantaged, light paraffin ($C_1$-$C_4$) feeds. Prior-art catalysts devised for this application usually contain an acidic zeolite material such as ZSM-5 and one or more metals such as Pt, Ga, Zn, Mo, etc. to provide a dehydrogenation function. Aromatization of ethane and other lower alkanes is thermodynamically favored at high temperature and low pressure without addition of hydrogen to the feed. Unfortunately, these process conditions are also favorable for rapid catalyst deactivation due to formation of undesirable surface coke deposits which block access to the active sites.

For many hydrocarbon processing applications, one approach to reducing catalyst performance decline rates due to coking is to increase the catalyst metals loading in an effort to promote faster hydrogenation/breakup of large coke precursor molecules on the surface. Another approach involves incorporation of additives such as phosphate or rare earths to moderate surface acidity and reduce coking rates under reaction conditions. These approaches are appropriate for processes featuring fixed or slowly-moving catalyst beds wherein the average catalyst particle residence time in the reactor zone between regenerations (coke burnoff steps) is relatively long (at least several days). For example, see U.S. Pat. Nos. 4,855,522 and 5,026,937, which describe ZSM-5-type lower-alkane aromatization catalysts promoted with Ga and additionally containing either a rare earth metal or a phosphorus-containing alumina, respectively.

Yet another approach to circumvent this problem is to devise a lower alkane aromatization process in which the catalyst spends a relatively short time (less than a day) under reaction conditions before being subjected to coke burnoff and/or other treatment(s) aimed at restoring all or some of the original catalytic activity. An example of such a process is one featuring two or more parallel reactors containing fixed or stationary catalyst beds, with at least one reactor offline for catalyst regeneration at any given time, while the other reactor(s) is/are processing the lower alkane feed under aromatization conditions to make aromatics. Another example of such a process features a fluidized catalyst bed, in which catalyst particles cycle rapidly and continuously between a reaction zone where aromatization takes place and a regeneration zone where the accumulated coke is burned off the catalyst to restore activity. For example, U.S. Pat. No. 5,053,570 describes a fluid-bed process for converting lower paraffin mixtures to aromatics.

Requirements for optimal catalyst performance in a process involving a relatively short period of catalyst exposure to reaction conditions between each regeneration treatment, such as a fluidized-bed process, can differ from those of fixed- or moving-bed processes which require longer catalyst exposure time to reaction conditions between regeneration treatments. Specifically, in processes involving short catalyst exposure times, it is important that the catalyst not exhibit excessive initial cracking or hydrogenolysis activity which could convert too much of the feedstock to undesirable, less-valuable byproducts such as methane.

Certain metals such as Pt which are very suitable for catalyzing the dehydrogenation reactions that are essential for an alkane dehydroaromatization process can also, under certain circumstances, display undesirable hydrogenolysis activity that leads to excessive production of methane from higher hydrocarbons. The inclusion of a second, inert or less-active metal in a catalyst composition to help suppress the hydrogenolysis activity of the first, more-active metal is used in commercial scale catalytic naphtha reforming in which $C_5$-$C_{12}$ paraffins and naphthenes are converted to aromatic compounds with catalysts which are predominantly bimetallic and are supported on chloride-promoted alumina. As indicated in a catalytic naphtha reforming review article by C. A. Querini in volume 6, pages 1-56 of the *Encyclopedia of Catalysis* (I. T. Horvath, ed.; published by John Wiley & Sons, Inc., Hoboken, N.J., USA, 2003), these catalysts typically contain Pt plus another metal such as Re (in sulfided form) or Sn. Among other effects, these second metals can interact with the Pt to reduce hydrogenolysis activity, thereby decreasing the rate of unwanted methane formation.

These Pt/Re and Pt/Sn catalysts, supported on chloride-promoted alumina, are widely employed in fixed-bed (semi-regenerative) and moving-bed (continuous) naphtha reformers, respectively, and their compositions are optimized for relatively long catalyst exposure times to reaction conditions between regeneration treatments. The average catalyst particle residence time in the reaction zone between regeneration treatments ranges from a few days in moving bed reactors and up to 1 or 2 years in fixed bed reactors. According to the article by Querini mentioned above, typical Pt and Sn levels in Pt/Sn naphtha reforming catalysts are 0.3% wt each. Such catalysts, which usually lack a strongly acidic zeolite component, do not work well for lower alkane aromatization.

It would be advantageous to provide a light hydrocarbon dehydroaromatization process which can be performed under conditions thermodynamically favorable for light alkane aromatization as described above, which provides for relatively short catalyst exposure time to reaction conditions, wherein the average catalyst particle residence time in the reaction zone between regeneration treatments may be from 0.1 second to 30 minutes in a fluidized bed reactor and from a few hours up to a week in moving bed and fixed bed reactors, and in which the catalyst composition is optimized to reduce excessive initial production of less-desirable byproducts such as methane.

SUMMARY OF THE INVENTION

The present invention provides a process for producing aromatic hydrocarbons which comprises:

(a) contacting ethane with a dehydroaromatization catalyst wherein the ethane contact time (the average residence time of a given ethane molecule in the reaction zone under reaction conditions) is preferably from 0.1 seconds to 1 minute, preferably 1 to 5 seconds, most preferably at 550 to 730° C. and 0.01 to 1.0 MPa, said catalyst comprising:
  (1) 0.005 to 0.1% wt (% by weight) platinum, basis the metal, preferably 0.01 to 0.06% wt, most preferably 0.01 to 0.05% wt,
  (2) an amount of iron which is equal to or greater than the amount of the platinum but not more than 0.50% wt of the catalyst, preferably not more than 0.20% wt of the catalyst, most preferably not more than 0.10% wt of the catalyst, basis the metal;
  (3) 10 to 99.9% wt of an aluminosilicate, preferably a zeolite, basis the aluminosilicate, preferably 30 to 99.9% wt, preferably selected from the group consisting of ZSM-5, ZSM-11, ZSM-12, ZSM-23, or ZSM-35, preferably converted to the H+ form, preferably having a $SiO_2/Al_2O_3$ molar ratio of from 20:1 to 80:1, and
  (4) a binder, preferably selected from silica, alumina and mixtures thereof;
(b) collecting the products from (a) and separating and recovering $C_{6+}$ aromatic hydrocarbons;
(c) optionally recovering methane and hydrogen; and
(d) optionally recycling $C_{2-5}$ hydrocarbons to (a).

The reactor system may comprise one or more reaction vessels, chambers, or zones, arranged in parallel or in series, in which contact between the catalyst particles and the ethane-containing feed occurs. The reactor vessel(s), chamber(s), or zone(s) may feature a fixed catalyst bed (i.e., with parallel beds), a slowly-moving catalyst bed, or a fluidized bed, In a preferred embodiment, a fluidized-bed reactor is used. The process is optimized to minimize the average catalyst particle residence time while maintaining selectivity and conversion rate. The average catalyst particle residence time is the average amount of time that a catalyst particle is in the active reaction zone with ethane between regenerations.

Catalysts of the present invention—featuring lower levels of dehydrogenation metal (preferably Pt) with potential cracking function, plus proper moderation of the dehydrogenation metal activity with appropriate amounts of a second, attenuating metal—are designed to limit initial cracking activity without sacrificing the overall activity and aromatics selectivity required for commercially-viable production rates of benzene and other aromatics.

DETAILED DESCRIPTION OF THE INVENTION

The present invention is a process for producing aromatic hydrocarbons which comprises bringing a hydrocarbon feedstock containing at least 50 percent by weight of ethane or other $C_2$ hydrocarbons into contact with a dehydroaromatization catalyst composition suitable for promoting the reaction of ethane to aromatic hydrocarbons such as benzene at a temperature of 550 to 730° C. and a pressure of 0.01 to 1.0 MPa. The primary desired products of the process of this invention are benzene, toluene and xylene.

The hydrocarbons in the feedstock may be ethane, ethylene or mixtures thereof. Preferably, the majority of the feedstock is ethane and from 0 to 20 weight percent of the feedstock may be comprised of ethylene, preferably 5 to 10 weight percent. The feedstock may contain in addition up to 40 weight percent of other open chain hydrocarbons containing between 3 and 8 carbon atoms as coreactants. Specific examples of such additional coreactants are propane, propylene, n-butane, isobutane, n-butenes and isobutene. The hydrocarbon feedstock preferably contains at least 60 percent by weight of $C_2$ hydrocarbons, more preferably at least 70 percent by weight. The reaction feed is often referred to herein as ethane for convenience but it is meant to include all of the other hydrocarbon materials referred to above if it is necessary or desired for them to be present.

In a preferred embodiment, the reactor comprises a zone, vessel, or chamber containing catalyst particles through which the ethane-containing feed flows and the reaction takes place. The reactor system may involve a fixed, moving, or fluidized catalyst bed. The reaction products then flow out of the bed and are collected. The reaction products are then separated and $C_{6+}$ aromatic hydrocarbons are recovered. Optionally, methane and hydrogen are recovered and optionally the $C_{2-5}$ hydrocarbons are recycled to step (a).

A fixed bed reactor is a reactor in which the catalyst remains stationary in the reactor and the catalyst particles are arranged in a vessel, generally a vertical cylinder, with the reactants and products passing through the stationary bed. In a fixed bed reactor the catalyst particles are held in place and do not move with respect to a fixed reference frame. The fixed bed reactor may be an adiabatic single bed, a multi-tube surrounded with heat exchange fluid or an adiabatic multi-bed with internal heat exchange, among others. Fixed bed reactors are also referred to as packed bed reactors. Fixed bed reactors provide excellent gas solids contacting. The fixed bed reactor configuration may include at least two separate fixed beds in different zones so that at least one bed can be in active operation under reaction conditions while the catalyst the other bed(s) is being regenerated.

In a moving bed catalytic reactor, gravity causes the catalyst particles to flow while maintaining their relative positions to one another. The bed moves with respect to the wall of the vessel in which it is contained. The reactants may move through this bed with cocurrent, countercurrent or crossflow. Plug flow is the preferred mode. The moving bed offers the ability to withdraw catalyst particles continuously or intermittently so they can be regenerated outside the reactor and reintroduced into the circuit later on. Thus, there is an advantage to using a moving bed when the catalyst has a short active life and can be continuously regenerated. A moving bed reactor may consist of at least one tray as well as supporting means for one or more catalyst beds. The supporting means may be permeable to gas and impermeable to catalyst particles.

A fluidized bed reactor is a type of reactor that may be used to carry out a variety of multiphase chemical reactions. In this type of a reactor, a gas is passed through the particulate catalyst at high enough velocities to suspend the solid and cause it to behave as though it were a fluid. The catalyst particles may be supported by a porous plate. The gas may be forced through the porous plate up through the solid material. At lower gas velocities the solids remain in place as the gas passes through the voids in the material. As the gas velocity is increased, the reactor reaches the stage where the force of the fluid on the solids is enough to balance the weight of the solid material and above this velocity the contents of the reactor bed begin to expand and swirl around much like an agitated tank or boiling pot of water. A fluidized bed reactor is preferred for use in the present invention because it provides uniform particle mixing, uniform temperature gradients and the ability to operate the reactor in a continuous state. The catalyst leaves the reaction zone with the reaction products and is separated therefrom in order to be regenerated before being recycled to the reaction zone.

The ethane contact time may range from 0.1 second to 1 minute. The ethane contact time is the average amount of time that one molecule of the ethane feed is in the reaction zone. The preferred ethane contact time is from 1 to 5 seconds. Longer ethane contact times are less desirable because they tend to allow for secondary reactions that lead to less-desirable byproducts such as methane and reduce selectivity to benzene and/or total aromatics.

The catalyst comprises from 0.005 to 0.1% wt platinum, basis the metal. The platinum is highly active in terms of catalyzing the dehydroaromatization reaction and it is best if its concentration in the catalyst not be more than 0.1% wt because otherwise too much methane will be produced. In one embodiment, from 0.01 to 0.06% wt platinum is used and most preferably, from 0.01 to 0.05% wt of platinum is used. High performance is thus obtained with relatively low amounts of metals in the catalyst.

An attenuating metal is an essential component of the catalyst of the present invention. The attenuating metal moderates the catalytic activity of platinum so as to reduce the production of less-valuable methane byproduct. The attenuating metal of the present invention is iron. For the present invention, the amount of the attenuating metal may be equal to or greater than the amount of platinum, preferably not more than 0.2% wt, more preferably not more than 0.10% wt of the attenuating metal is utilized in the catalyst because more than that can cause the overall conversion to aromatics to become too low for commercial use.

The catalyst also comprises from 10 to 99.9% wt of one or more aluminosilicate materials, preferably from 30 to 99.9% wt, basis the aluminosilicate(s). The aluminosilicates preferably have a silicon dioxide:aluminum trioxide molar ratio of from 20 to 80. The aluminosilicates may preferably be zeolites having the MFI or MEL type structure and may be ZSM-5, ZSM-8, ZSM-11, ZSM-12 or ZSM-35. The zeolite or zeolite mixture is preferably converted to $H^+$ form to provide sufficient acidity to help catalyze the dehydroaromatization reaction. This can be accomplished by calcining the ammonium form of the zeolite in air at a temperature of at least 400° C.

The binder material serves the purpose of holding individual zeolite crystal particles together to maintain an overall catalyst particle size in the optimal range for fluidized-bed operation or to prevent excessive pressure drop in fixed or moving bed operation. The binder may be selected from the group consisting of alumina, silica, silica/alumina, various clay materials such as kaolin, or mixtures thereof. Preferably, amorphous inorganic oxides of gamma alumina, silica, silica/alumina or a mixture thereof may be included. Most preferably, alumina and/or silica are used as the binder material.

A platinum containing crystalline aluminosilicate, such as ZSM-5, may be synthesized by preparing the aluminosilicate containing the aluminum and silicon in the framework, depositing platinum on the aluminosilicate and then calcining the aluminosilicate. The attenuating metal may also be added by the same procedure, either prior to, simultaneously with, or after the addition of platinum. The metals may be added by any commonly known method for adding metals to such structures including incorporation into the aluminosilicate framework during crystal synthesis, or subsequent ion exchange into an already-synthesized crystal framework, or well as by various impregnation methods known to those skilled in the art. The platinum and attenuating metal may be added by the same or different methods.

In a preferred embodiment of the present invention an ethane feedstream is introduced into the dehydroaromatization reactor. The feedstream then comes into contact with the catalyst particles for the prescribed period of time. The reaction products leave the reactor and are transferred into a separator. The separator removes the aromatic products and the principal byproducts, methane and hydrogen, which preferably may be recovered, and also removes $C_{2-5}$ byproducts and unreacted ethane which optionally may be recycled to the dehydroaromatization reactor.

EXAMPLE

The following example is illustrative only and is not intended to limit the scope of the invention.

Example 1

Catalysts A through D were prepared on samples of ZSM-5 zeolite powder CBV 3024E (30:1 molar $SiO_2:Al_2O_3$ ratio), available from Zeolyst International. The powder samples were calcined in air up to 650° C. to remove residual moisture prior to use in catalyst preparation.

Metals were deposited on 25-50 gram samples of the above calcined ZSM-5 powder substrate by first combining appropriate amounts of stock solutions of tetraamine platinum nitrate and ammonium ferric oxalate, diluting this mixture with deionized water to a volume just sufficient to fill the pores of the substrate, and impregnating the substrate with this solution at room temperature and atmospheric pressure. Impregnated samples were aged at room temperature for 2-3 hours and then dried overnight at 100° C.

Target platinum levels for catalysts A, B, and C were all 0.04% wt. The target platinum level for catalyst D was 0.15% wt. Target iron levels for catalysts A, B, C, and D were 0, 0.04, 0.08, and 0.15% wt, respectively. The platinum and iron contents of catalyst D were determined by first calcining a sample of the catalyst at 550° C. to drive off residual moisture and render a loss on ignition (LOI) percentage. A known mass of untreated, ground catalyst D, corrected by LOI percentage, was digested using closed vessel microwave acid digestion involving nitric, hydrochloric, and hydrofluoric acids. The solution was diluted to a known volume with deionized water, then analyzed for platinum and iron by directly coupled plasma emission analysis. The results of duplicate analyses were 0.160 and 0.165% wt for platinum (average value 0.1625% wt) and 0.174 and 0.170% wt for iron (average value 0.172% wt). These results are expressed as weight percent based on the weight of the 550° C.-calcined catalyst sample.

Catalysts made on the ZSM-5 substrate were first loaded into plastic bags and pressed at 20,000 psig for 2 min using an isostatic press. The resulting "rock" was then crushed and sieved to obtain 2.5-8.5 mm particles suitable for testing. For each performance test, a 15-cc charge of catalyst was loaded into a quartz tube (1.40 cm i.d.) and positioned in a three-zone furnace connected to an automated gas flow system.

Prior to performance testing, all catalyst charges were pre-treated in situ at atmospheric pressure as follows:
 (a) calcination with air at 60 liters per hour (L/hr), during which the reactor wall temperature was increased from 25 to 510° C. in 12 hrs, held at 510° C. for 4-8 hrs, then further increased from 510 to 630° C. in 1 hr, then held at 630° C. for 30 min;
 (b) nitrogen purge at 60 L/hr, 630° C. for 20 min;
 (c) reduction with hydrogen at 60 L/hr, 630° C. for 30 min.

At the end of the pretreatment, 100% ethane feed was introduced at 15 L/hr (1000 gas hourly space velocity-GHSV), atmospheric pressure, with the reactor wall temperature maintained at 630° C. The total reactor outlet stream was sampled and analyzed by an online gas chromatography system two minutes after ethane feed addition. Based on composition data obtained from the gas chromatographic analysis, initial ethane conversion and hydrocarbon product selectivities were computed according to the following formulas:

ethane conversion, %=100×(100−% wt ethane in outlet stream)/(% wt ethane in feed)

selectivity to hydrocarbon product $Y$ (other than ethane)=100×(moles of carbon in amount of product $Y$ generated)/(moles of carbon in amount of ethane reacted)

For purposes of the selectivity calculation, $C_{9+}$ aromatics were assumed to have an average molecular formula of $C_{10}H_8$ (naphthalene).

Analyzed platinum and tin levels and initial aromatization performance data for Catalysts A-D, prepared and tested as described above, are presented in Table 1. The data in Table 1 indicate that the low-Pt/Fe/ZSM-5 catalysts B and C of the present invention (less than 0.05% wt Pt, Fe level greater than the amount of Pt but not above 0.10% wt) provide better initial suppression of methane production and higher selectivity to benzene and total aromatics under ethane aromatization conditions than catalysts A and D, in which the Pt/Fe levels fall outside the ranges of the present invention.

TABLE 1

| Catalyst | A | B | C | D |
|---|---|---|---|---|
| Target Pt Level, % wt | 0.04 | 0.04 | 0.04 | 0.15 |
| Target Fe Level, % wt | 0 | 0.04 | 0.08 | 0.15 |
| Ethane conversion, % | 60.39 | 58.03 | 50.89 | 68.52 |
| Selectivities, % (carbon basis) | | | | |
| Methane | 38.09 | 32.12 | 24.24 | 41.25 |
| Ethylene | 6.52 | 7.1 | 7.95 | 3.58 |
| Propylene | 0.7 | 0.9 | 1.13 | 0.61 |
| Propane | 0.7 | 0.86 | 1.3 | 0.45 |
| C4 Hydrocarbons | 0.14 | 0.16 | 0.21 | 0.14 |
| C5 Hydrocarbons | 0 | 0 | 0.01 | 0 |
| Benzene | 33.3 | 36.02 | 36.51 | 30.49 |
| Toluene | 16.32 | 16.79 | 18.8 | 14.05 |
| C8 Aromatics | 2.75 | 2.6 | 3.63 | 2.44 |
| C9+ Aromatics | 1.49 | 3.45 | 6.22 | 6.99 |
| Total Aromatics | 53.85 | 58.85 | 65.16 | 53.97 |

What is claimed is:

1. A process for producing aromatic hydrocarbons which comprises:
   (a) contacting ethane with a dehydroaromatization catalyst in a reactor for 0.1 seconds to 1 minute, said catalyst comprising:
      (1) 0.005 to 0.1% wt platinum, basis the metal,
      (2) an amount of iron which is equal to or greater than the amount of the platinum, basis the metal, but not more than 0.50% wt of the catalyst;
      (3) 10 to 99.9% wt of an aluminosilicate, and
      (4) a binder;
   (b) collecting the products from (a) and separating and recovering $C_{6+}$ aromatic hydrocarbons,
   (c) optionally recovering methane and hydrogen; and
   (d) optionally recycling $C_{2-5}$ hydrocarbons to (a).

2. The process of claim 1 wherein the reactor comprises a bed of catalyst particles and the ethane flows through the bed.

3. The process of claim 2 wherein the reactor is selected from fixed bed, moving bed, and fluidized bed reactors.

4. The process of claim 1 wherein the ethane is contacted with the catalyst for from 1 to 5 seconds.

5. The process of claim 1 wherein the reaction is carried out at from 550 to 730° C. and from 0.01 to 1.0 MPa.

6. The process of claim 1 wherein the amount of platinum is from 0.01 to 0.05% wt.

7. The process of claim 1 wherein the catalyst comprises not more than 0.10% wt of iron.

8. The process of claim 1 wherein the amount of the aluminosilicate is from 30 to 99.9% wt.

9. The process of claim 1 wherein the aluminosilicate has a silicon dioxide:aluminum trioxide molar ratio of from 20 to 80.

10. The process of claim 1 wherein the aluminosilicate is a zeolite.

11. The process of claim 10 wherein the zeolite is selected from the group consisting of ZSM-5, ZSM-11, ZSM-12, ZSM-23, and ZSM-35.

* * * * *